(12) United States Patent
Gleich et al.

(10) Patent No.: US 8,355,771 B2
(45) Date of Patent: Jan. 15, 2013

(54) METHOD OF DETERMINING A SPATIAL DISTRIBUTION OF MAGNETIC PARTICLES

(75) Inventors: Bernhard Gleich, Hamgburg (DE); Jurgen Weizenecker, Hamburg (DE); Tim Nielsen, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 1570 days.

(21) Appl. No.: 11/721,371

(22) PCT Filed: Dec. 6, 2005

(86) PCT No.: PCT/IB2005/054073
§ 371 (c)(1),
(2), (4) Date: Jun. 11, 2007

(87) PCT Pub. No.: WO2006/064405
PCT Pub. Date: Jun. 22, 2006

(65) Prior Publication Data
US 2009/0240135 A1    Sep. 24, 2009

(30) Foreign Application Priority Data

Dec. 15, 2004 (EP) .................................. 04106608

(51) Int. Cl.
*A61B 5/05* (2006.01)
(52) U.S. Cl. ........................................ 600/409; 600/410

(58) Field of Classification Search ................ 424/9.32, 424/451; 600/407–409, 410, 420; 324/301, 324/302, 200–263, 307, 309; 607/103
See application file for complete search history.

(56) References Cited

U.S. PATENT DOCUMENTS

| 4,136,683 A | 1/1979 | Gordon |
| 6,082,366 A | 7/2000 | Andra et al. |
| 2003/0085703 A1* | 5/2003 | Gleich .................. 324/309 |

FOREIGN PATENT DOCUMENTS

| DE | 10151778 | 5/2003 |
| EP | 0095124 | 11/1983 |
| WO | 2004091397 | 10/2004 |

* cited by examiner

*Primary Examiner* — Tse Chen
*Assistant Examiner* — Joel F Brutus

(57) ABSTRACT

The invention relates to a method of determining a spatial distribution of magnetic particles in an examination zone, in which a magnetic field is generated that has a first sub-zone of lower magnetic field strength and a second sub-zone of higher magnetic field strength. The positions of the two sub-zones are changed, as a result of which the magnetization in the examination zone changes. Measured values that depend on the change in magnetization are acquired. A reference response function by means of which measured values can be determined mathematically from a spatial distribution of magnetic particles is then determined by means of at least extensive magnetic specimen distribution. Finally, the spatial distribution of magnetic particles is reconstructed from the measured values by means of the reference response function.

16 Claims, 4 Drawing Sheets

METHOD OF DETERMINING A SPATIAL DISTRIBUTION OF MAGNETIC PARTICLES

The invention relates to a method of determining a spatial distribution of magnetic particles in an examination zone. The invention also relates to an apparatus for performing the method according to the invention and to a computer program for controlling the apparatus according to the invention.

A method of the kind specified in the opening paragraph is known from DE 101 51 778. In the method described there, a magnetic field is first generated in such a way that a first sub-zone of lower magnetic field strength and a second sub-zone of higher magnetic field strength are produced in the examination zone, i.e. the magnetic field strength in the first sub-zone is lower than it is in the second sub-zone. The positions in space of the sub-zones in the examination zone are then changed, thus causing a local change in the magnetization of the particles in the examination zone. Signals are acquired that are dependent on the magnetization in the examination zone, which is affected by the change in the positions in space of the sub-zones, information on the spatial distribution of the magnetic particles in the examination zone being obtained from these signals to enable an image to be generated of the examination zone. In DE 101 51 778, it is proposed that an image of the examination zone be reconstructed by applying to the signals measured a back-convolution operation with a magnetization function that is dependent on the magnetization characteristic of the magnetic particles.

A disadvantage of this known method is the fact that the reconstruction produces images of the examination zone whose quality is often not sufficiently good for, for example, a diagnosis in medical applications.

It is therefore an object of the present invention to specify a method of the kind outlined in the opening paragraph in which the quality of the image generated is improved.

This object is achieved by a method of determining a spatial distribution of magnetic particles in an examination zone having the following steps a) generation of measured values by the following steps
  generation of a first magnetic field having a pattern of magnetic field strength in space such that a first sub-zone of lower magnetic field strength and a second sub-zone of higher magnetic field strength are produced in the examination zone,
  changing the positions in space of the sub-zones in the examination zone, thus causing a local change in the magnetization of the particles,
  acquisition of measured values that depend on the magnetization in the examination zone, which has been affected by the change in the positions of the two sub-zones,
b) provision of a reference response function by means of which measured values can be determined mathematically from a spatial distribution of magnetic particles, the reference response function being determined by means of at least one extensive magnetic specimen distribution,
c) reconstruction of the spatial distribution of magnetic particles in the examination zone from the measured values by means of the reference response function provided.

In contrast to the prior art described above, there is provided in accordance with the invention a reference response function by means of which measured values can be determined mathematically from a spatial distribution of magnetic particles. A response function of this kind is also sometimes referred to as a response function of the measuring system and simulates the generation of the measured values in step a), i.e. application of the response function to a spatial distribution of magnetic particles in the examination zone gives simulated measured values. The reference response function is described in more detail below, particularly in connection with equation (1).

In determining the reference response function, use is made of an extensive magnetic specimen. In the context of the invention, the term "extensive" refers to the size of the magnetic specimen. A magnetic specimen is extensive when it is larger than what is termed a delta specimen. A delta specimen is a quantity of magnetic particles that is confined to as small as possible a region of space, but which is nevertheless sufficiently large to enable, if there is a change in the positions in space of the first and second sub-zones, measured values to be acquired that are sufficiently large for them to be distinguishable from values for the noise to which the method according to the invention is subject, and that are therefore suitable for reconstruction purposes. Also, the delta specimen is preferably sufficiently small for its diameter to be less than the resolution, which is preset by the measuring process, in the reconstructed image, said resolution being equal to the minimum distance between two magnetic particles in the examination zone at which the two particles can still be shown separately in the reconstructed image. The diameter of an extensive magnetic specimen is for example at least 0.5 mm.

Compared to the use of a delta specimen, the determination according to the invention of the reference response function by means of an extensive magnetic specimen results in the change in the positions of the first and second sub-zones causing a greater change in the magnetization, as a result of which, as will be explained in detail below, a reference response function of better quality is determined. If a reference response function of better quality of this kind is used for the reconstruction of an image of the examination zone, this also improves the quality of the reconstructed image as compared with the method specified in the second paragraph.

As will be explained in detail below, the generation of the measured values in step a) can be seen as a convolution of the spatial distribution of magnetic particles in the examination zone with the reference response function. A reference response function of good quality can therefore be generated, if a known specimen distribution of magnetic particles is positioned at different points in the examination zone, if measured values for the specimen are generated for each position of the specimen distribution in the examination zone, and if the reference response function is determined by de-convoluting the reference response function from the specimen distribution with the help of the measured values for the specimen.

In an embodiment a way of de-convoluting the reference response function that calls for only a small amount of computation is described.

In an embodiment, a transformation that includes a Fourier transformation, i.e. the said transformation comprises a Fourier transformation amongst other things, is applied to the measured values for the specimen, i.e. to measured values that are acquired when an extensive specimen distribution is situated in the examination zone and step a) is performed, and the measured values for the specimen are transformed in such a way that the number of transformed measured values for the specimen is smaller than the number of non-transformed measured values for the specimen. This is for example useful if, at certain time-frequencies, Fourier transformed measured values for the specimen are so large that they can be distinguished from noise, i.e. from values for the noise to which the measuring system by which the method according to the invention is performed is subject, whereas at other time-frequencies they are so small they cannot be distinguished from the noise of the measuring system. In this case, ranges of time-frequencies in which the temporally Fourier transformed measured values for the specimen are so small that they cannot be distinguished from the noise of the measuring system may be situated between time-frequencies at which the temporally Fourier transformed measured values for the specimen are so large than they can be distinguished from the noise of the measuring system. Also, it is possible that measured values for the specimen have only a given band of time-frequencies, e.g. due to the filtering properties of the measuring system, which will mean that after a temporal Fourier transformation all the temporally Fourier transformed measured values for the specimen that lie outside this band of time-frequencies will be so small that they cannot be distinguished from the noise of the measuring system. Temporally Fourier transformed measured values for the specimen that are so small that they cannot be distinguished from the noise of the measuring system will be ignored in succeeding steps according to the invention. In one embodiment, the transformation claimed in claim 4 therefore comprises the temporal Fourier transformation of the measured values for the specimen and subsequent ignoring of Fourier transformed measured values for the specimen that are so small as to be indistinguishable from the noise of the measuring system. A reduction of this kind in the number of measured values for the specimen results in a reduction in the computing work when the reference response function is de-convoluted.

In an embodiment, a plurality of spatially extensive specimen distributions that have different space-frequencies are used for the determination of the reference response function, the specimen distributions being of a form such that measured values for the specimen that are larger than the noise values caused by the method according to the invention, and by the apparatus according to the invention by which the method is performed, are generated for each space-frequency in one or more preset ranges of space-frequencies. If a reference response function determined in the manner claimed in claim 5 is used to reconstruct the spatial distribution of magnetic particles in step c), the quality of the reconstructed image of the examination zone will be further improved.

In an embodiment, matching values are determined in addition to the measured values for the specimen by matching trigonometric functions to the measured values for the specimen. To de-convolute the reference response function, use is then made either of only the matching values or of both the measured values for the specimen and the matching values. The use of the matching values gives a further improvement in the quality of the reference response function and hence in the quality of the spatial distribution of magnetic particles that is, in the end, reconstructed.

In an embodiment datasets are formed, each dataset containing solely temporally Fourier transformed measured values for the specimen of one time-frequency and the data in the given dataset depending on the point at which the specimen distribution was positioned in the examination zone while the particular measured value for the specimen was being generated. It has been found that datasets that have Fourier transformed measured values for the specimen of a higher time-frequency have higher space-frequencies than datasets that have Fourier transformed measured values for the specimen of a lower time-frequency. If therefore, in an embodiment as claimed in claim 8, what are used to determine matching values for a dataset that has temporally Fourier transformed measured values for the specimen of a higher time-frequency are trigonometric functions that have a higher space-frequency than trigonometric functions that are used to determine matching values for a dataset that has temporally Fourier transformed measured values for the specimen of a lower time-frequency, then there will be a further improvement in the quality of the reference response function and hence in the quality of the spatial distribution of magnetic particles that is reconstructed in step c).

In an embodiment, after the measured values for the specimen have been generated, intermediate measured values are determined, the intermediate measured values corresponding to measured values for the specimen that would have been measured if, when the measured values for the specimen were being generated, the specimen distribution had been positioned at a point that was located at a point intermediate between those points in the examination zone at which the specimen distribution was actually positioned during the generation of the measured values for the specimen. What are then used to de-convolute the reference response function are both the measured values for the specimen and the intermediate values, as a result of which there is a further improvement in the quality of the reference response function and the quality of the spatial distribution of magnetic particles that is reconstructed in step c).

In an embodiment, a transfer function is provided that, when applied to measured values for the specimen that were measured while the specimen distribution was positioned at a point in the examination zone, gives transfer values that correspond to measured values for the specimen that would have been measured if the specimen distribution had been located at some other point in the examination zone. This transfer function may for example be provided by taking advantage of known symmetries of the measuring apparatus. In this way it may for example be known that measured values for the specimen that are measured while the specimen distribution is situated in one region of the examination zone are equal to the measured values for the specimen that are measured when the specimen distribution is situated in another region of the examination zone. Fewer measured values for the specimen may for example then be needed for de-convoluting the reference response function, because additional transfer values are determined by means of the transfer function. Hence the measuring time is shortened in this way. Alternatively, while the number of measured values for the specimen remains the same, the transfer values may be used as an addition for the de-convolution, which increases the signal-to-noise ratio, which in turn gives a further improvement in the quality of the reference response function and the quality of the distribution of magnetic particles in the examination zone that is reconstructed in step c).

The use of a delta specimen as a specimen distribution would have the disadvantage that, due to the small quantity of magnetic particles, the measured values acquired would have a low signal-to-noise ratio. A delta specimen would however have the advantage that, because the spatial Fourier transform of a delta specimen is a constant in the space-frequency domain, the spatial Fourier transform of the spatial distribution of magnetic particles that is to be reconstructed in step c) would be reconstructed to an equally good quality for different space-frequencies. Therefore, as claimed in claim 11, it is first determined how high the field strengths are, at different points in the examination zone, of the first magnetic field and of a second magnetic field that is variable with time and that is used to change the position in space of the two sub-zones (301, 302). These field strengths correspond to the field strengths that would act on a delta specimen that was positioned at the points concerned. The extensive specimen distribution is then positioned at any desired point in the examination zone and measured values for the specimen are determined for each of the different fields strengths determined. Because the same field strengths act on the extensive specimen distribution as would act on a delta specimen that was positioned at different points in the examination zone, a reconstruction in step c) using a reference response function that is de-convoluted with these measured values for the specimen will result in the spatial Fourier transform of the reconstructed image of the examination zone being reconstructed to an equally good quality at different space-frequencies, as a result of which there is a further improvement in the quality of the spatial distribution of magnetic particles that is reconstructed in step c).

Pieces of apparatus for performing the method according to the invention are described. In an embodiment, a computer program for controlling an apparatus is disclosed. In an embodiment a computer program for controlling an apparatus is disclosed. In an embodiment, a method of determining a reference response function for a method according to the invention of determining the spatial distribution of magnetic particles.

These and other aspects of the invention are apparent from and will be elucidated with reference to the embodiments described hereinafter.

Figure 1:
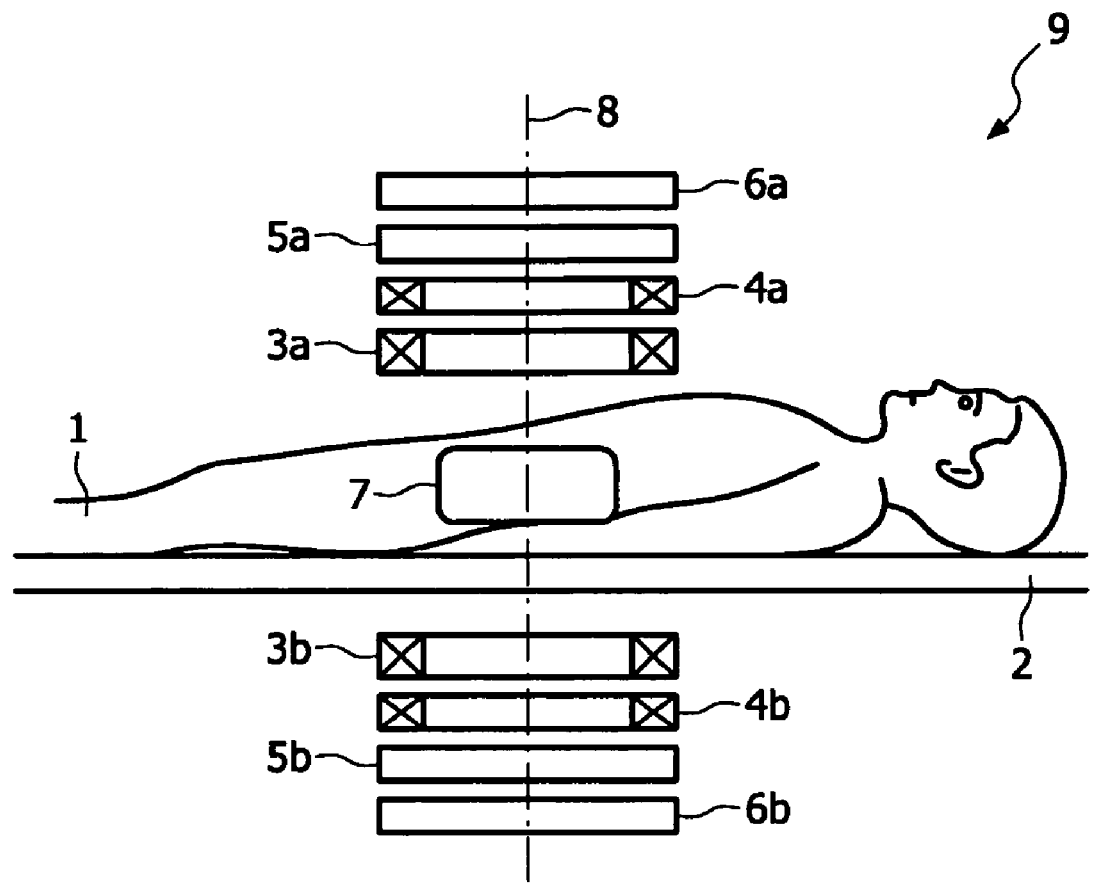
FIG. 1 is a schematic representation of an apparatus according to the invention for performing the method according to the invention.

An embodiment of an apparatus 9 according to the invention is shown in FIG. 1. Situated on a patient presentation table 2 is an object, which in the present case is a patient 1. Situated in the patient 1, in the gastro-intestinal tract for example, and in an examination zone of the apparatus 9, are magnetic particles that were administered to the patient in, for example, a liquid or meal form. As will be explained below, the size of the examination zone depends in particular on the magnetic fields and the magnetic particles that are used.

Figure 2:
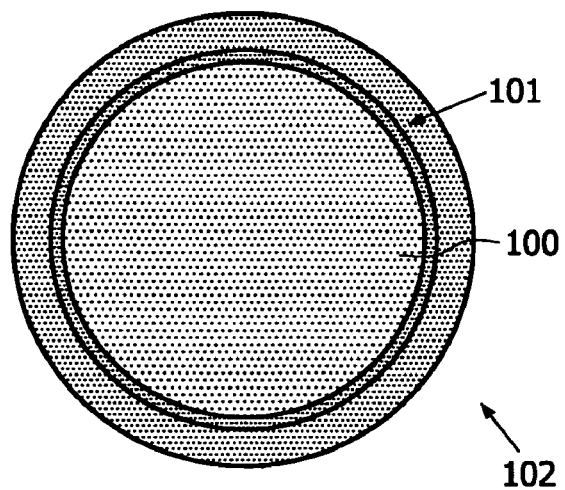
FIG. 2 shows one of the magnetic particles present in the examination zone.

A magnetic particle is shown in FIG. 2. It comprises a spherical substrate 100, of glass for example, that is coated with a soft-magnetic layer 101 that is for example 5 nm thick and is for example composed of an iron-nickel alloy (e.g. Permalloy). This layer may for example be overlaid with a covering layer 102 that protects the particle against acid. The strength of the magnetic field required to saturate the magnetization of such particles depends on the diameter of the particles. For a diameter of 10 μm, a magnetic field of 1 mT is required for this purpose, whereas for a diameter of 100 μm a magnetic field of 100 μT is all that is required. If the coating selected has a lower saturation magnetization than Permalloy, then there is of course a further reduction in the magnetic field required for saturation.

For the sake of simplicity, the field strengths specified in the context of the invention are given in Teslas. This is not entirely correct because the Tesla is the unit of magnetic flux density. To obtain the magnetic field strength in the given case, the value that is given also has to be divided by the magnetic field constant $\mu_0$.

The invention is not limited to the magnetic particle that has just been described. Rather, the method according to the invention can be performed with any magnetic particle that has a non-linear magnetization characteristic, i.e. for which the curve followed by the magnetization of the magnetic particle as a function of the magnetic field strength acting on the particle is not linear.

What may also be used are so-called mono-domain particles made of ferromagnetic or ferrimagnetic material. The dimensions of these particles are in the nanometer range and they are so small that no magnetic domains, i.e. Weiss domains, are able to form in them. They can be injected into a patient's blood stream in a suitable colloidal dispersion. In the magnetic resonance field (MR field), dispersions of this kind are already being injected as a contrast medium. The size of the magnetic particles used in this field is 5 to 10 nm. This however is not the optimum size for the method according to the invention because the magnetic field strength required for saturation decreases as the third power of the particle diameter. The magnetic particles should therefore be as large as possible, but not so large that magnetic domains are able to form. Depending on the magnetic material, the figure for the optimum size of a mono-domain magnetic particle is between 20 and 800 nm. A material suitable for mono-domain particles is for example magnetite ($Fe_3O_4$). Such particles may for example be inhaled for examinations of the lungs.

In the context of the invention, the term "magnetic particles" also includes particles that are magnetizable.

Above and below the patient 1 is situated a first pair of coils 3a, 3b (first magnetic means), which comprises two coils 3a, 3b of identical construction that are arranged co-axially above and below the patient 1 (See FIG. 1) and through which flow currents of the same size but of different directions of circulation, and which generate a first magnetic field that is constant over time.

Figure 3:
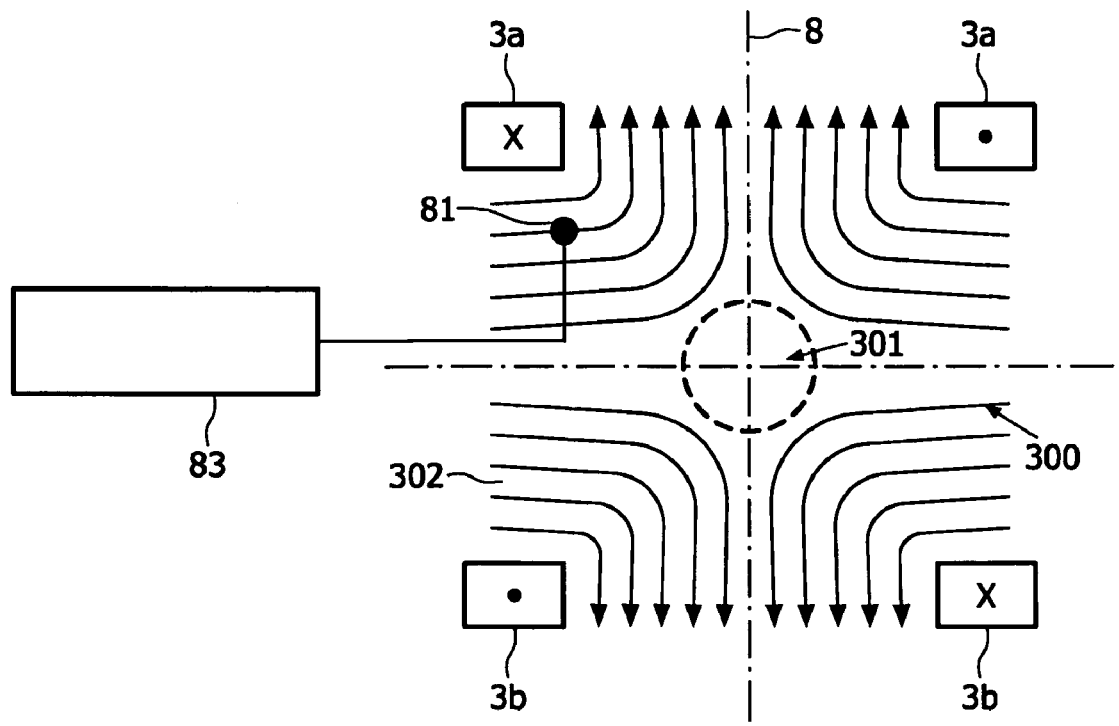
FIG. 3 shows the pattern of field-lines in a first magnetic field that is constant over time in the apparatus of FIG. 1.

The first magnetic field is represented in FIG. 3 by means of the field lines 300. Its gradients are almost constant in the direction of the common axis 8 of the coils, and it reaches a value of zero at a point on this coil axis. Starting from this point at which there is no field, the strength of the magnetic field increases in all directions in space with increasing distance. In a first sub-zone 301, which is indicated by a dashed line in FIG. 3 and is located around the point at which the field is zero, the strength of the first magnetic field is so low that the magnetization of particles situated in it is not saturated. In a second sub-zone 302 on the other hand, which is situated outside the first sub-zone 301, the magnetization of the magnetic particles is saturated.

The sample distribution 81 that is also shown in FIG. 3, and the positioning means 83 for positioning the specimen distribution 81 in the examination zone, are used only for determining the reference response function, and they are therefore not situated in the examination zone while measured values for determining the distribution in the examination zone of magnetic particles, which are situated for example in the gastro-intestinal tract of a patient, are being acquired. The determination of the reference response function by means of the specimen distribution 81 and the positioning means 83 will be explained in detail below. The first sub-zone 301 of the first magnetic field can be shifted in the examination zone by means of a second magnetic field that is variable over time.

The movement and dimensions of the first sub-zone 301, and the magnetic properties and distribution of the magnetic particles, determine the size of the examination zone. Every region of the object to be examined, i.e. of the patient 1 for example, that has magnetic particles whose magnetization is changed due to the change in position of the first sub-zone 301 is contained in the examination zone.

To generate the second magnetic field that is variable over time, three further pairs of coils (second magnetic means) are provided. The pair of coils 4a, 4b generates a component of the second magnetic field that extends in the direction of the axis 8 of the first pair of coils 3a, 3b. For this purpose, the coils 4a, 4b have currents of the same size flowing through them in the same direction of circulation. In principle, the effect achievable with the pair of coils 4a, 4b could also be achieved by superimposing currents in the same direction on the equal currents in opposite directions in the first pair of coils 3a, 3b, as a result of which the current would decrease in one pair of coils and increase in the other pair of coils.

To generate components of the second magnetic field in directions that are oriented perpendicularly to the axis of the pair of coils 3a, 3b, use is made of two further pairs of coils 5a, 5b and 6a, 6b. Like the pairs of coils 3a, 3b and 4a, 4b, these pairs of coils 5a, 5b and 6a, 6b could be of the Helmholtz type, though if they were the examination zone would be surrounded by the pairs of coils in all three directions in space, which would make access to the examination zone more difficult. Coils 5a, 6a are therefore arranged above the patient 1 and coils 5b, 6b below the patient 1. The coils 5a, 5b generate a component of the magnetic field the direction of which is oriented perpendicularly to the coil axis 8. Also, the coils 6a, 6b generate a magnetic field component whose direction is oriented perpendicularly to the coil axis 8 and perpendicularly to the direction of the magnetic field component that is generated by the pair of coils 5a, 5b. The coils 5a, 5b and 6a, 6b thus generate magnetic field components that are oriented perpendicularly to their axis. Coils of this kind are not of the Helmholtz type and are known from magnetic resonance units having open magnets ("open MRI") in which a pair of high-frequency coils that is able to generate a horizontal magnetic field variable over time is arranged above and below the patient. The construction of these known coils 5a, 5b, 6a, 6b will not be explained in detail here.

The pairs of coils 4a, 4b . . . 6a, 6b thus generate the second magnetic field that is variable over time and by means of which the first sub-zone 301 of the first magnetic field can be moved in the examination zone, which latter is three-dimensional in the present case but, as an alternative, may also be one-dimensional or two-dimensional. The movement of the first sub-zone 301 in the examination zone results in a change in the magnetization of the magnetic particles 102, by which means signals are induced in a suitable receiving coil. The relationship between the movement of the first sub-zone 301 and the changing magnetization of the magnetic particles and the induced signals that result therefrom is explained in detail in DE 101 51 778, the description of which is hereby incorporated by reference.

There is shown in schematic form in FIG. 1 a receiving coil 7 (acquisition means) that is so adapted that signals (measured values) can be induced in said receiving coil 7 due to changing magnetization in the examination zone. In principle, each of the pairs of field-generating coils 3a, 3b . . . 6a, 6b could also be used for this purpose. One, or even more than one, separating receiving coil or coils 7 have however the advantage that they can be arranged and switched independently of the field-generating coils 3a, 3b . . . 6a, 6b and give an improved signal-to-noise ratio. The induction of signals in the receiving coil 7 due to the change in the magnetization of the magnetic particles 102 is described in more detail in DE 101 51 778, the description of which is also hereby incorporated by reference at this point.

If the change in magnetization is to be acquired in all three directions in space, then for each direction in space there will be required at least one receiving coil that is able to receive the component in the corresponding direction of the change in magnetization.

Figure 4:
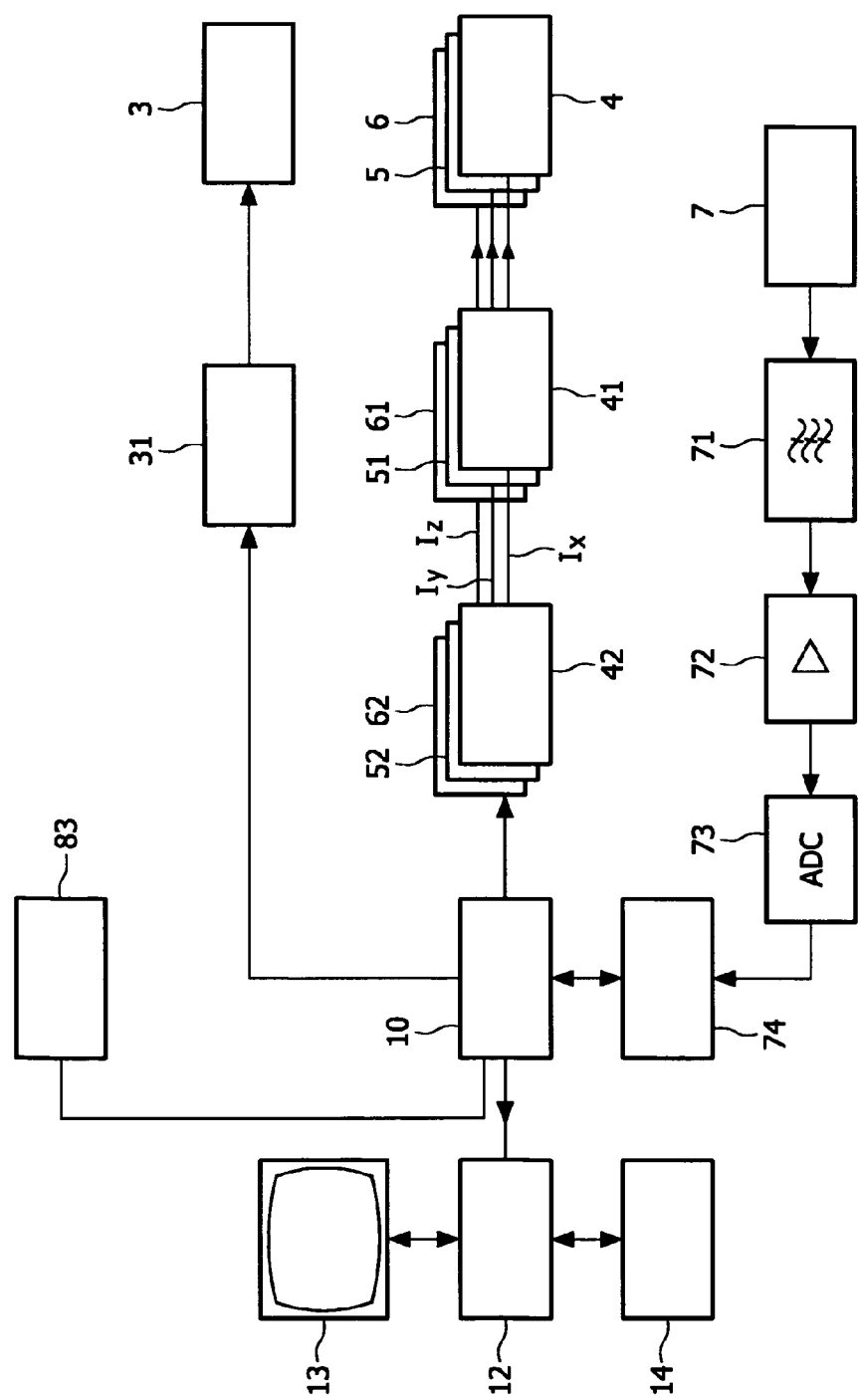
FIG. 4 is a block circuit diagram of the apparatus of FIG. 1.

FIG. 4 is a block circuit diagram of the apparatus 9 shown in FIG. 1. The pair of coils 3a, 3b is shown schematically in FIG. 4 and for reason of clarity is denoted by reference numeral 3. The same is true of the pairs of coils 4a, 4b . . . 6a, 6b.

The pair of coils (first magnetic means) 3 is supplied by a controllable current source 31 with a d.c. current that is controlled by a control unit 10. The control unit 10 is connected to a computer 12 having a monitor 13 to display the distribution of magnetic particles in the examination zone and having an input unit 14, such as a keyboard 14 for example. The control unit 10 is also connected to positioning means 83, thus enabling the control unit 10 to arrange the specimen distribution 81 at different points in the examination zone by means of the positioning means 83. The positioning means 83 may for example be a robot arm controlled by the control unit 10, which can be moved as desired within the examination zone.

The pairs of coils (second magnetic means) 4, 5, 6 are connected to current amplifiers 41, 51, 61 from which they receive their currents. The current amplifiers 41, 51, 61 are connected in turn to respective a.c. current sources 42, 52, 62 that preset the waveform over time of the currents to be amplified $I_x$, $I_y$, $I_z$. The a.c. current sources 42, 52, 62 are controlled by the control unit 10.

Also shown schematically in FIG. 4 is the receiving coil (acquisition means) 7. The signals induced in the receiving coil 7 are fed to a filter unit 71 by which the signals are filtered. The purpose of this filtering is to separate measured values that are caused by the magnetization in the examination zone that is affected by the change in position of the two sub-zones (301, 302) from other, interfering signals. For this purpose, the filter unit 71 may for example be of a form such that signals having time-frequencies that are lower than the time-frequencies at which the pairs of coils 4, 5, 6 are operated, or than twice these time-frequencies, will not pass through the filter unit 71. The signals are then transmitted via an amplifier unit 72 to an analog-to-digital converter (ADC) 73. The digitized signals generated by the analog-to-digital converter 73 are fed to an image processing unit (reconstruction means) 74 and this reconstructs the spatial distribution of the magnetic particles from these signals and from the position at the time that the first sub-zone 301 of the first magnetic field had assumed in the examination zone during the reception of the relevant signal, which position the image processing unit 74 receives from the control unit 10. Finally, the reconstructed spatial distribution of the magnetic particles is transmitted via the control unit 10 to the computer 12, which displays it on the monitor 13.

For the determination, as described below, of the reference response function, the control unit 10 transmits to the image processing unit 74 the point $\vec{y}_i$ at which the extensive specimen distribution 83 has been arranged by means of the positioning means 81.

Also, as is explained in detail below, measured values for the specimen are measured, and these too are transmitted via the control unit 10 to the image processing unit 74. The image processing unit 74 them calculates the reference response function from the measured values for the specimen and the known specimen distribution that is stored in the image processing unit 74.

Figure 5:
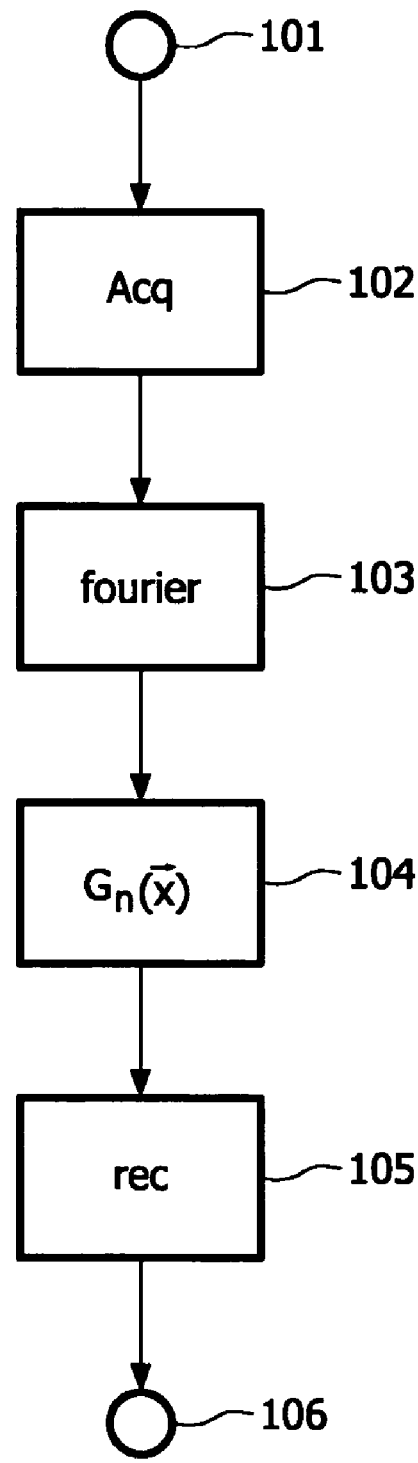
FIG. 5 is a flow chart of a method according to the invention.

FIG. 5 is a flow chart of a method according to the invention that can be performed with the apparatus shown in FIG. 1 and FIG. 4.

After initialization in step 101, the coils 3a, 3b generate the first magnetic field having the two sub-zones 301 and 302.

In step 102, the positions of the two sub-zones 301 and 302 in the examination zone are changed by the time-variable second magnetic field. The second magnetic field is in this case of a form such that the first sub-zone 301 moves in the examination zone along a path that is of a form such that the entire examination zone is covered by the first sub-zone 301. Because of the movement of the two sub-zones 301 and 302 in the examination zone, there is a change in the magnetization of magnetic particles in the examination zone. Before the method is performed, these magnetic particles are introduced into the examination zone by, for example, a patient having swallowed magnetic particles in the form of a meal to allow the gastro-intestinal tract to be examined. The changing magnetization of the magnetic particles in the examination zone produces induced signals in the receiving coil 7, i.e. measured values that are measured continuously over time by the above-described apparatus 9.

Alternatively, the change in the position in space of the two sub-zones 301 and 302 in the examination zone could also be produced without a second magnetic field by moving the examination zone, which could be done by moving the patient presentation table 2 on which the patient 1 is lying for example. What is more, the examination zone and the two sub-zones 301 and 302 could also be moved simultaneously as a result of the second magnetic field. What is important is that the positions of the two sub-zones 301 and 302 change relative to the examination zone.

In step 103, the measured values are transformed by means of a temporal Fourier transformation in such a way that the number of transformed measured values is smaller than the number of non-transformed measured values for the specimen. For this purpose the measured values are first Fourier transformed temporally. Then, in the subsequent steps, temporally Fourier transformed measured values that cannot be distinguished from the noise of the measuring system are ignored, thus reducing the computing work and storage requirements in the subsequent steps.

Because of the electrical components that are used, the apparatus 9 according to the invention has filtering properties. The frequency band of the measured values acquired is limited by the properties of the magnetic particles, by their size for example. There are thus fewer temporally Fourier transformed measured values that are sufficiently large to be distinguishable from the noise of the measuring system than there are measured values that are not temporally Fourier transformed, which means that the computing work in the subsequent steps in which the temporally Fourier transformed measured values are used is reduced. By a procedure of this kind, measured values that do not make any contribution to improving the quality of the image are ignored in the reconstruction.

If the filtering properties of the system as a whole, i.e. the filtering properties that are determined by the apparatus 9 according to the invention and by properties of the magnetic particles, are known, from measurements that have already been made for example, then in other embodiments allowance could be made for the limited range of time-frequencies of the measured values acquired by ignoring certain measured values in the subsequent steps without a temporal Fourier transformation being performed. If for example the highest frequency measured is detectable at a sampling rate in time (signals measured per unit of time) that is only half as large as the sampling rate used during the acquisition in step 102, then each pair of actual measured values that are adjacent in time may be replaced by their mean value. Alternatively, it is also possible in this case for only every second actual measured value to be looked at in the subsequent steps.

Also, time-frequency ranges in which the temporally Fourier transformed measured values for the specimen are so small as to be indistinguishable from the noise of the measuring system may be situated between time-frequencies at which the temporally Fourier transformed measured values for the specimen are so large that they are distinguishable from the noise of the measuring system. In this case too, the temporally Fourier transformed measured values that are looked at in the subsequent steps will be only those that are sufficiently large to be distinguishable from the noise.

In step 104 a reference response function is determined. By means of a reference response function, measured values can be determined mathematically from a spatial distribution of magnetic particles. The reference response function therefore defines the relationship between the spatial distribution $C(\vec{x})$ of magnetic particles in the examination zone and the measured values. In the present embodiment the measured values were temporally Fourier transformed in step 103. In the present case, the temporally Fourier transformed reference response function $G_n(\vec{x})$ having the time-frequency $\omega_n$ therefore defines the relationship between the temporally Fourier transformed measured value $V_n$ having the time-frequency $\omega_n$ and the spatial distribution $C(\vec{x})$ of magnetic particles in accordance with the following equation:

$$V_n = \S G_n(\vec{x}) C(\vec{x}) d\vec{x} \tag{1}$$

In this case the integration variable $\vec{x}$ traverses the entire examination zone. The time-frequencies $\omega_n$ are those time-frequencies at which the temporally Fourier transformed measured values are so large as to be distinguishable from the noise of the measuring system. The subscript n thus designates the $n^{th}$ time-frequency of those time-frequencies of the temporally Fourier transformed measured values that are still looked at after the transformation in step 103.

To allow the reference response function to be determined, the magnetic particles are removed from the examination zone, i.e. generally the patient is removed from the examination zone, and an extensive magnetic specimen distribution is positioned, with the positioning means 83, at different successive points $\vec{y}_i$ in the examination zone. In the context of the invention, an extensive specimen distribution is for example a compact magnetic specimen, such as a cylinder or a sphere for example, which is not a delta specimen. The specimen distribution may also have magnetic particles arranged in a grid-like pattern and in this way magnetic particles may be arranged at intersections of an imaginary grid or along lines of a grid.

If the specimen distribution is arranged at a point $\vec{y}_i$, the sub-zones 301 and 302 are moved relative to the examination zone, by the second magnetic field in this case, in exactly the same way as they are during the measurement in step 102. The signals induced in the receiving coil are measured and are temporally Fourier transformed as in step 103. These measured signals are referred to as measured values for the specimen. The specimen distribution is positioned at each point $\vec{y}_i$ in the examination zone, and measured values for the specimen are acquired for each point $\vec{y}_i$.

The points $\vec{y}_i$ at which the specimen distribution is positioned are preferably arranged at intersections of a Cartesian grid that are evenly distributed over the entire examination zone. Adjoining points $\vec{y}_i$ may for example be situated at a distance of 1 mm from one another.

The temporally Fourier transformed measured value $W_n(\vec{y}_i)$ for the specimen, having the time-frequency $\omega_n$, that was acquired while the specimen distribution was arranged at the point $\vec{y}_i$ can be defined by the following equation:

$$W_n(\vec{y}_i) = \int G_n(\vec{s}+\vec{y})P(\vec{s})d\vec{s} \quad (2)$$

In the equation, the position vector $\vec{s}$ is referred to a co-ordinate system, e.g. a Cartesian co-ordinate system, that has a fixed connection to the specimen distribution $P(\vec{s})$. The origin of this co-ordinate system is arranged at that given point in the examination zone that is designated by $\vec{y}$.

Under equation (2), the temporally Fourier transformed measured values for the specimen $W_n(\vec{y}_i)$ are a convolution of the temporally Fourier transformed reference response function with the specimen distribution. To allow the reference response function to be determined, the temporally Fourier transformed reference response function must therefore de-convoluted from the specimen distribution by means of the measured values for the specimen, the reference response function being obtained after a temporal Fourier back-transformation.

The following equation is obtained by spatial Fourier transformation of equation (2):

$$\hat{W}_n(\vec{k}) = \hat{G}_n(\vec{k})\hat{P}^*(\vec{k}) \quad (3)$$

In this equation, $\hat{W}_n(\vec{k})$ is the spatial Fourier transform, having the space-frequency $\vec{k}$, of the temporal Fourier transform, having the time-frequency $\omega_n$, of the measured values for the specimen. Similarly, $\hat{G}_n(\vec{k})$ is the spatial Fourier transform, having the space-frequency $\vec{k}$, of the temporal Fourier transform, having the time-frequency $\omega_n$, of the reference response function. Finally, $\hat{P}^*(\vec{k})$ is the complex conjugated spatial Fourier transform, having the space-frequency $\omega_n$, of the specimen distribution.

The reference response function is therefore de-convoluted from the specimen distribution by means of the measured values for the specimen by spatially Fourier transforming the temporally Fourier transformed measured values for the specimen, and the specimen distribution, in accordance with equation (3), by complex conjugating the spatially Fourier transformed specimen distribution, and by dividing the given Fourier transform $\hat{W}_n(\vec{k})$ by the given complex conjugated spatial Fourier transform $\hat{P}^*(\vec{k})$ of the specimen distribution for each space-frequency $\vec{k}$ and each time-frequency $\omega_n$. Finally, the values $\hat{G}_n(\vec{k})$ obtained from the division are spatially Fourier back-transformed, thus giving the temporally Fourier transformed reference response function $G_n(\vec{x})$.

The quotient $\hat{W}_n(\vec{k})/\hat{P}^*(\vec{k})$ is referred to in the context of the invention as the quotient function.

In step 105, an image of the examination zone is reconstructed from the measured values that were acquired in step 102 and transformed in step 103, by means of the reference response function determined in step 104, i.e. the distribution of magnetic particles in the examination zone, which distribution was for example present in the gastro-intestinal tract of a patient during the measurement in step 102, is reconstructed.

Because the reference response function is known, the reconstruction may be performed in different known ways that, by taking account of equation (1) and with known temporally Fourier transformed measured values Vn and the known temporally Fourier transformed reference response function $G_n(\vec{x})$, enable the distribution $C(\vec{x})$ of magnetic particles in the region of examination to be determined. In the present embodiment the distribution of magnetic particles is determined by minimizing the following expression $$\sum_n \left| V_n - \sum_j G_n(\vec{x}_j)C(\vec{x}_j)\Delta\vec{x} \right|, \quad (4)$$

i.e. the distribution $C(\vec{x})$ is adjusted using known adjusting algorithms in such a way that the expression (4) is a minimum, with the expression | ... | designating the amount. In this case, the outer sum covers all the time-frequencies $\omega_n$ that are considered after step 103. Furthermore, the inner sum covers all the points $\vec{x}_j$ in the examination zone for which the temporal Fourier transform of the reference response function was determined in step 104. The term $\Delta\vec{x}$ is the distance between two successive points $\vec{x}_j$ in the examination zone.

If expression (4) is a minimum, then the distribution $C(\vec{x})$ of magnetic particles in the examination zone has been reconstructed and the method according to the invention end at steps 106.

If the reference response function, and hence the temporally Fourier transformed reference response function too, have been determined for a give movement of the first sub-zone 301 relative to the examination zone, i.e. for a given second magnetic field that is variable over time, then with subsequent measurements that, in step 102, make use of the same movement of the first sub-zone 301 relative to the examination zone, the distribution of magnetic particles in the examination zone can, after the transformation in step 103, be determined directly in step 105, in which case the temporally Fourier transformed reference response function determined previously can be used.

Therefore, even before measured values are acquired in step 102, the reference response function can be determined in step 104 for different movements of the first sub-zone 301 relative to the examination zone, i.e. for different second magnetic fields, and can be stored in the image processing unit 74. If an unknown distribution of magnetic particles in the examination zone is to be reconstructed, then one of the movements for which a reference response function has been determined can be selected, the measured values then being acquired in steps 101 and 102 with this movement and transformed in step 103, and the distribution of magnetic particles being reconstructed in step 105 by means of the known reference response function.

It is within the scope of the invention for step 103 to be dispensed with. What this means it that it is not necessary for the measured values to be temporally Fourier transformed. If step 103 is dispensed with, the result of this is of course that the measured values for the specimen are also not temporally Fourier transformed in step 104 and that everything that has been said about a temporal Fourier transform of measured values, of measured values for the specimen or of the reference response function relates to the measured values themselves, the measured values for the specimen themselves or the reference response function itself. Also, when this is the case, there is not of course any temporal Fourier back-transformation after the de-convoluting of the reference response function.

A particularly good reference response function is obtained in preset space-frequency ranges if what are used for determining the reference response function are measured values for the specimen that, for each space-frequency within the preset ranges of space-frequencies, are larger than the values for the noise that is caused by the apparatus according to the invention and the method according to the invention.

To preset a range of space-frequencies, the measured values acquired in step 102 are spatially Fourier transformed, and it is determined at what space-frequencies the spatially Fourier transformed measured values are different from the values for noise, i.e. at what space-frequencies the spatially Fourier transformed measured values are larger than the values for noise. The range or ranges of space-frequencies are preset in such a way that they comprise all or most of the space-frequencies that were determined in this way.

If it is known even before the measurement in step 102 at what space-frequencies spatially Fourier transformed measured values are distinguishable from values for noise, then one or more ranges of space-frequencies can be preset in such way that they comprise all or most of these space-frequencies. This pre-knowledge may for example be the result of previous measurements made with similar distributions of magnetic particles. If for example the gastro-intestinal tract is examined in different adults, it can be assumed that, for different adults, spatially Fourier transformed measured values that are distinguishable from values for noise will be situated in the same ranges of space-frequencies. What is more, the range or ranges of space-frequencies may also be determined on the basis of mathematical considerations. If for example the movement of a catheter, which catheter is indicated by a circular distribution of magnetic particles of a diameter of 1 mm, is to be tracked in the examination zone, then this distribution will produce measured values whose spatial Fourier transform is distinguishable from values for noise in a range of space-frequencies from 0 to $2\pi$ mm$^{-1}$, which means that this range of space-frequencies will be preset.

To generate, for each space-frequency within the preset range or ranges of space-frequencies, spatially Fourier transformed measured values for the specimen that are larger than values for noise caused by the apparatus according to the invention and the method according to the invention, what are preferably used, as described below, are a plurality of specimen distributions.

Values are first determined for noise. The determination of values for noise for a piece of measuring apparatus is known to the person skilled in the art. Values for noise may for example be determined by performing the measurement of the measured values for the specimen described in step 104, including the movement of the positioning means 83, without a specimen distribution being present in the examination zone. The values acquired are then dependent not on the magnetization in the examination zone that is affected by the change in the positions of the two sub-zones, but on the noise of the method according to the invention and the apparatus according to the invention.

For each positioning of the positioning means 83 which corresponds to a position of a specimen distribution in step 104, a value for noise is determined by forming a mean over a preset period of time, which is done by squaring the values acquired, integrating the squared values over the preset period of time, dividing the resulting integral value by the preset period of time and finally taking the square root of the resulting quotient. The preset period of time will be sufficiently large that a longer period of time would not cause any change in the value for noise. In this way, a value for noise is determined for each position of the positioning means 83 that corresponds to a position of a specimen distribution in the examination zone in step 104, which value for noise is thus position-dependent. This position-dependent value for noise is spatially Fourier transformed, thus giving for each space-frequency a spatially Fourier transformed value for noise that is used for comparison with the measured values for the specimen of the same space-frequency. As already mentioned, other methods known to the person skilled in the art may also be used to determine value for noise for a measuring apparatus in the context of the invention. In this way, allowance may for example also be made for the power spectrum when determining the values for noise.

Once values for noise have been determined, a first specimen distribution that has space-frequencies that are situated in at least one preset range of space-frequencies is arranged in the examination zone. If for example a range of space-frequencies from 0 to $2\pi$ mm$^{-1}$ has been preset, then what may first be used is a grid-type specimen distribution having a grid-line spacing of 2 mm. Measured values for the specimen are then measured in the way described in step 104 and those space-frequencies are determined, in the preset range or ranges of space-frequencies, at which the spatially Fourier transformed measured values for the specimen cannot be distinguished from the values for noise, i.e. at which the spatially Fourier transformed measured values for the specimen are not larger than the relevant values for noise. The first specimen distribution is then removed for the examination zone and a second specimen distribution is arranged in it, the second specimen distribution having a grid-type structure having a spacing between the grid-lines that corresponds to a space-frequency at which the measured values for the specimen that were determined by means of the first specimen distribution are no larger than the values for noise. Measured values for the specimen are then again measured, and it is determined at what space-frequencies, in the preset range or ranges of space-frequencies, spatially Fourier transformed measured values for the specimen for the first and second specimen distributions are no large than values for noise. Using further specimen distributions, which are likewise grid-type distributions but have different grid-line spacings, spatially Fourier transformed measured values for the specimen that can be distinguished from values for noise are determined for these space-frequencies. Hence, measured values for the specimen are measured for different specimen distributions until such time as spatially Fourier transformed measured values for the specimen that are larger than values for noise have been determined for all the space-frequencies lying within the range or ranges of space-frequencies.

For each of these specimen distributions, a preliminary reference response function or a temporally Fourier transformed preliminary reference response function is determined in step 104, all the preliminary reference response functions being combined into a reference response function that is used for the reconstruction in step 105. The different preliminary reference response functions may be combined by for example forming their arithmetic mean. If for example a temporally Fourier transformed reference response function $G_n^v(\vec{x})$ has been determined for each specimen distribution, then for example the arithmetic mean may be formed of the temporally Fourier transformed preliminary reference response functions that have been determined for the different specimen distributions, for each time-frequency $\omega_n$ and each point $\vec{x}$ in the examination zone for example, with the resulting mean value being the value of the temporally Fourier transformed reference response function that has been determined for the time-frequency $\omega_n$ concerned and the point $\vec{x}$ concerned. If the measured values for the specimen are not temporally Fourier transformed, then the reference response function $G_t(\vec{x})$ dependent on time t can be determined in a corresponding way by forming a mean.

In the combining of the preliminary reference response functions for different specimen distributions, the values of the different preliminary reference response functions are differently weighted when the mean is formed. If, for a space-frequency, a mean is formed of values of preliminary reference response functions, or of values of temporally Fourier transformed preliminary reference response functions, of different specimen distributions, then the values of the different preliminary reference response functions or temporally Fourier transformed reference response functions are multiplied by a weighting factor and then added together. In this case the weighting factor for a preliminary reference response function, or a temporally Fourier transformed reference response function, of a space-frequency is all the larger the large is the spatially Fourier transformed measured value for the specimen for the space-frequency and for that specimen distribution for which the particular preliminary reference response function has been determined.

To increase the quality of the reference response function $G_t(\vec{x})$ or of the temporally Fourier transformed reference response function $G_n(\vec{x})$ (if $G_n(\vec{x})$ has been determined, then $G_t(\vec{x})$ too is known, and vice versa, because they can be changed into one another by a temporal Fourier transformation), then in other embodiments according to the invention matching values and/or intermediate values and/or transfer values may be determined that can be used, alone or together with the measured values for the specimen, to de-convolute the reference response function from the specimen distribution $P(\vec{s})$.

To determine the matching values, the measured values for the specimen are temporally Fourier transformed, if this has not already been done. Then, a linear combination of trigonometric functions is matched to each of temporally Fourier transformed measured values for the specimen, of the same time-frequency, that are dependent on the point at which the specimen distribution was positioned when the given measured value for the specimen was measured.

The matching is preferably performed by first re-sorting the measured values for the specimen in such a way that temporally Fourier transformed measured values for the specimen of the same time-frequency form a dataset in each case. In each dataset, the particular temporally Fourier transformed measured values for the specimen are then dependent only on the given position of the specimen distribution in the examination zone. In each dataset, a linear combination of trigonometric functions is matched to the temporally Fourier transformed measured values for the specimen, with the space-frequency of the trigonometric functions being all the higher the higher is the time-frequency of the temporally Fourier transformed measured values for the specimen in the given dataset. The linear combination $F_n(\vec{y})$ of trigonometric functions that is used in the given dataset for matching to the temporally Fourier transformed measured values for the specimen of the time-frequency $\omega_n$ may for example be defined by the following equation:

$$F_n(\vec{y}) = \sum_{\vec{k} \in \{\vec{k}_n, \Delta\vec{k}_n\}} a(\vec{k})\sin(\vec{k} \cdot \vec{y}) + b(\vec{k})\cos(\vec{k} \cdot \vec{y}). \tag{5}$$

In this equation, $\{\vec{k}_n, \Delta\vec{k}_n\}$ is a set of space-frequencies that comprises a space-frequency $\vec{k}_n$ and space-frequencies shifted by $\Delta\vec{k}_n$ and $-\Delta\vec{k}_n$ relative to $\Delta\vec{k}_n$.

One possible way of determining the space-frequency $\vec{k}_n$ is for the generation of the measured values for the specimen to be simulated. The specimen distribution and the physical processes that produce the measured values for the specimen are known, and this means that imaginary measured values for the specimen can be calculated that, although they are unable to allow for all the specific peculiarities of the measuring apparatus 9 and the specimen distribution, and particularly the magnetic properties of the latter, and are therefore not suitable for the direct determination of the reference response function, are nevertheless sufficiently good for determining the space-frequency $\vec{k}_n$. The imaginary measured values for the specimen are temporally Fourier transformed and re-sorted in such a way that imaginary measured values for the specimen of one space-frequency that have been temporally Fourier transformed form a dataset in each case. Each dataset is then spatially Fourier transformed and the greatest amplitude of the spatially Fourier transformed data in the dataset is determined, the space-frequency at which the spatially Fourier transformed data is at a maximum being the space-frequency $\vec{k}_n$.

A further possible way of determining the space-frequency $\vec{k}_n$ is for the given dataset of the measured values for the specimen that have been measured to be spatially Fourier transformed and for the space-frequency $\vec{k}_n$ to be determined in the way that has just been described for the simulated dataset. This possible procedure will be successful whenever the space-frequency $\vec{k}_n$ is not under-sampled in the given dataset.

The vector $\Delta\vec{k}_n$ is preset. In the matching, $\Delta\vec{k}_n$ also makes allowance for space-frequencies that differ only slightly from the space-frequency $\vec{k}_n$. What this means is that the size of $\Delta\vec{k}_n$ is preferably small in comparison with the size of the space-frequency $\vec{k}_n$. It may even be equal to zero.

Alternatively, $\Delta\vec{k}_n$ can also be determined from the temporally and spatially Fourier transformed imaginary measured values for the specimen or from measured values for the specimen that have been measured, by using for $\Delta\vec{k}_n$ the vector of the distance between the given space-frequency $\vec{k}_n$ in the given dataset and the space-frequency at which the spatial Fourier transform of the given dataset has its second-largest amplitude.

The amplitudes $a(\vec{k})$ and $b(\vec{k})$ are matching parameters in equation (5).

The matching of the given linear combination $F_n(\vec{y})$ to the temporally Fourier transformed measured values for the specimen in the given dataset can be performed with any known matching algorithm, for example by finding the least-square fit.

Instead of the vectors $\vec{k}_n$ and $\Delta\vec{k}_n$ being preset, they may also be used as additional matching parameters in the matching.

What are used for de-convoluting the reference response function are for example only the matching values $F_n(\vec{y})$ obtained from the matching. Alternatively, what may also be used are the matching values and the measured values for the specimen. If matching values and measured values for the specimen are used together, then the given matching value $F_n(\vec{y})$ alone can be used at the points $\vec{y}$ at which the specimen distribution is not positioned in step 104. At points $\vec{y}$ at which the specimen distribution is positioned in step 104, it is preferred for a mean to be formed of the matching value $F_n(\vec{y})$ and the associated measured value for the specimen, this mean then being used for de-convoluting the reference response function, as a result of which the signal-to-noise ratio of the values used for the de-convolution is increased.

As an alternative or in addition, in other embodiments intermediate values are also used for de-convoluting the reference response function. For the determination of the intermediate values, the measured values for the specimen are not temporally Fourier transformed. The non-temporally Fourier transformed measured value for the specimen that was measured at a time t while the specimen distribution was positioned at a point $\vec{y}_i$ is designated $W_t(\vec{y}_i)$.

If the measured values acquired in step 102 and the measured values for the specimen are not temporally Fourier transformed, then the subscript n should be replaced in equations (1) to (4) by the subscript t. These equations and the associated descriptions therefore apply, mutatis mutandis, to measured values acquired in step 102 that are not temporally Fourier transformed and to measured values for the specimen acquired in step 104.

An intermediate value is a measured value for the specimen that would have been measured if the specimen distribution had been positioned, when the measured values for the specimen were generated, at a point $\vec{z}_t$ that was arranged between the points $\vec{y}_i$ in the examination zone at which the specimen distribution was actually positioned during the generation of the measured values for the specimen.

To determine an intermediate value for an intermediate point $\vec{z}_t$ of this kind, what are looked at are measured values for the specimen that were measured while the specimen distribution was situated at points $\vec{y}_i$ in the examination zone that are adjacent to the intermediate point $\vec{z}_t$.

If, during the acquisition of the measured values for the specimen, the first sub-zone 301 approaches a region in the examination zone at which the density of the magnetic particles in the specimen distribution is higher, there is a rise in the signal measured, i.e. the measured values rise in this way. If the first sub-zone 301 moves away again from this region, the signal declines again. Hence, when a region in which the density of the magnetic particles in the specimen distribution is higher is crossed, a delta-shaped surge in the signal is acquired, i.e. a measured value surge. This measured value surge is not of course delta-shaped in the mathematical sense, i.e. infinitely thin and infinitely high, but has a finite width and height. If for example the specimen distribution comprises a magnetizable sphere, the measured values will rise when the first sub-zone 301 approaches the sphere and will fall again when the first sub-zone 301 moves away again from the sphere.

Once a distribution of intermediate points has been preset, by for example laying it down that there is always an intermediate point $\vec{z}_t$ situated between each two most closely adjacent points $\vec{y}_i$, the intermediate values are determined for each point $z_t$ at which the specimen distribution is imagined to be positioned.

To determine intermediate value surges for an intermediate point $\vec{z}_j$, what are taken into account are measured value surges that were measured while the specimen distribution was arranged at points that are located adjacent the particular intermediate point $\vec{y}_i$. If the specimen distribution is for example a spherical distribution, if this specimen distribution was arranged at the adjacent positions 1 and 2 in succession and if, for the determination of an intermediate value, the specimen distribution is imagined to be arranged at a position 3 that is centrally located between positions 1 and 2, then the measured values for the specimen that are taken into account are ones that were acquired while the sub-zone 301 was passing over position 1 when the specimen distribution was positioned at position 1, and while the first sub-zone 301 was passing over position 2 when the specimen distribution was positioned at position 2.

As has already been mentioned above, for determining intermediate value surges for an intermediate point $\vec{z}_j$, the measured values for the specimen that are taken into account are ones that were acquired while the specimen distribution was arranged at points in the examination zone that are located adjacent to the intermediate point. In the present embodiment, the measured values for the specimen that are taken into account are those that were measured while the specimen distribution was located at the two neighboring points that are the shortest distance away from the intermediate point.

The points in time are first determined at which the intermediate values surges that are to be determined are at an extreme. For this purpose, those points in time are determined at which the measured value surges for the specimen that were measured while the specimen distribution was located at the first neighboring point were at an extreme. Then, those points in time are determined at which the measured value surges for the specimen that were measured while the specimen distribution was located at the second neighboring point were at an extreme. The points in time at which the intermediate value surges that are to be determined are at their extremes each lie between, and in particular centrally between, a point in time at which a measured value surge for the specimen that was measured while the specimen distribution was located as the first neighboring point was at an extreme, and a point in time at which a measured value surge for the specimen that was measured while the specimen distribution was located as the second neighboring point was at an extreme.

For each determined point in time at which the intermediate value surge to be determined is at an extreme, the height and half-value width of the associated intermediate value surge are determined by forming, in particular arithmetically, the means of the height and half-value width of a temporally adjacent measured value surge for the specimen that was measured while the specimen distribution was arranged at the first neighboring point, and of the height and half-value width of a temporally adjacent measured value surge for the specimen that was measured while the specimen distribution was arranged at the second neighboring point. Alternatively, a ratio may also be found between the height and half-value width of the intermediate value surges by simulation. If this ratio is known, then means could be formed of those areas of the particular temporally adjacent measured value surges for the specimen that are cut off below itself by each measured value surge for the specimen, the measured value surge for the specimen being of a form such that it is of the mean area and has the ratio between its height and half-value width that was determined by simulation.

To simulate the intermediate value surge, the specimen distribution is imagined to be positioned at the given intermediate point and the given intermediate value surge is calculated by taking into account the known physical processes that take place. Although these calculated intermediate value surges cannot take account of all the peculiarities of the measuring apparatus 9 and of the specimen distribution, and particularly the magnetic properties of the latter, they are still sufficiently accurate to give a usable ratio between the height and half-value width of the intermediate value surges. The physical processes that have to be taken into account are described in DE 101 51 778.

An intermediate value surge can also be determined for a point in time by shifting a temporally adjacent measured value surge for the specimen that was acquired while the specimen distribution was positioned at the first neighboring point, and a temporally adjacent measured value surge for the specimen that was acquired while the specimen distribution was positioned at the second neighboring point, over the top of one another so that the points in time at which the measured value surges for the specimen are at their extremes are on top of one another. A mean is then formed, in particular mathematically, of the measured value surges for the specimen that were shifted over the top of one another and the resultant mean measured value surge for the specimen is then a determined intermediate value surge and is shifted in such a way that the extreme of this measured value surge for the specimen is situated at the point in time for which the intermediate value surge is to be determined. Alternatively, more than two temporally adjacent measured value surges for the specimen may be shifted over the top of one another and a mean then formed of them.

The intermediate values determined are used in addition to the measured values for the specimen for the de-convolution of the reference response function in step 104, as a result of which the quality of the reference response function, and hence the quality of the image of the examination zone that is reconstructed in step 105, are improved.

As an alternative to, or in addition to, the matching values and/or the intermediate values, transfer values are determined in a further embodiment according to the invention.

Transfer values are determined by means of a transfer function that is provided and that is for example stored in the image processing unit 74. If is applied to measured values for the specimen that were measured while the specimen distribution was situated at a given point in the examination zone, this transfer function gives imaginary measured values for the specimen that would have been measured if the specimen distribution had been situated at some other point in the examination zone. A transfer function thus establishes a connection between different points or zones in the examination zone.

The transfer function can be preset by considering the first and second magnetic fields. If for example the first and second magnetic fields are known at a first point and a second point in the examination zone then, because the physical processes that result in the measured values for the specimen are known, from DE 101 51 778 for example, measured values for the specimen that would have been measured if the specimen distribution had been situated at the first point can be calculated from measured values for the specimen that were measured while the specimen distribution was situated at the second point. The transfer function covers this calculation, so by applying the transfer function to the measured values for the specimen that were measured while the specimen distribution was situated at the second point, measured values for the specimen can be determined that would have been measured if the specimen distribution had been situated at the first point. If for example, the first magnetic field is the same at different points in the examination zone, due to properties of symmetry that the measuring apparatus 9 has, then, if the first sub-zone 301 moves across both points in the same way, the measured values for the specimen that are generated at these points will also be the same, which means when this is the case the transfer function, when applied to a measured value for the specimen that was measured at the one point will give, for the other point, a transfer value that is equal to the measured value for the specimen at this point.

If a transfer function is preset that establishes a connection between a plurality of points in the examination zone, then in step 104 the specimen distribution will be positioned only at points $\vec{y}_i$, in the examination zone for which a connection to other points in the examination zone is not established by the transfer function, and it will be for these points $\vec{y}_i$ that measured values for the specimen are generated. Of the points in the examination zone between which a connection is established by the transfer function, the specimen distribution will be positioned only at one such point and, if measured values for the specimen have been measured for this point, transfer values will be determined for the correlated points by means of the transfer function. The measured values for the specimen that are measured and the transfer values will then be used to de-convolute the reference response function in step 104. The measuring time is reduced by a procedure of this kind Alternatively, the specimen distribution is positioned at each point $\vec{y}_i$, in the examination zone and measured values for the specimen are generated for each such point in the way described in step 104. In addition, transfer values are generated by means of the transfer function, and both measured values for the specimen and transfer values thus exist for each point $\vec{y}_i$, or for a plurality of point $\vec{y}_i$, in the examination zone. If both a measured value for the specimen and also one or more transfer values exist for a point $\vec{y}_i$, in the examination zone at which the specimen distribution is positioned, and also for a point in time t or for a time-frequency $\omega_n$ if temporally Fourier transformed values are being considered, then a mean will be formed of these measured and transfer values, mathematically for example, to give one value, and this value will be used for the de-convolution of the reference response function, as a result of which there will be a further improvement in the quality of the reference response function and hence in the quality of the distribution of magnetic particles that is to be reconstructed in step 105.

The transfer function also makes allowance for the sensitivity of the receiving coil 7. If a specimen distribution is positioned first at a first point in the examination zone and then at a second point in the said zone, an ideal receiving coil would give the same measured values for the specimen in both cases (unless of course the measured values for the specimen in question were acquired at different times, because the sub-zone 301 moves across the specimen distribution at different times). In the real world however, this is not the case. The receiving coil 7 is not ideal in this sense. The sensitivity profile of the receiving coil 7 indicates how those measured values for the specimen will differ that were measured when the specimen distribution was situated at different points in the examination zone and that would have been the same if an ideal receiving coil had been used. The sensitivity profile may for example comprise sensitivity factors that give the ratio by which measured values for the specimen differ that would be the same if an ideal receiving coil were used. The transfer function allows for these sensitivity factors by multiplying the transfer values that would be obtained with an ideal receiving coil by the given sensitivity factor.

In what follows, an embodiment according to the invention will be described in which, in step 104, to allow the reference response function to be determined, the specimen distribution is not positioned at different points in the examination zone.

The field strength of the first magnetic field is first determined at those points $\vec{y}_i$ at which the specimen distribution $\vec{y}_i$ is positioned in the embodiments described above. The field strength at these points is either known or can be measured there by means of for example a Hall probe.

The strength of the second magnetic field that is used to change the positions in space of the two sub-zones (301, 302) in step 102, which strength is variable over time, is then determined at the points $\vec{y}_i$ at which the strength of the first magnetic field was determined. This field strength too, including its variation over time, is either known or can be measured at the point in question by means of for example a Hall probe.

The extensive specimen distribution is then positioned at any desired point in the examination zone, preferably in the center of the examination zone.

Next, measured values for the specimen are generated for each point $\vec{y}_i$, by generating a homogeneous magnetic field of the strength that was determined at the point in question for the first magnetic field, which is done by generating a magnetic field that is variable over time of the time-variable strength determined for the point in question and by acquiring measured values for the specimen with the receiving coil.

The measured values for the specimen that were measured at a given determined field strength for the first magnetic field and a given determined time-dependent field strength for the second magnetic field are assigned to the point $\vec{y}_i$, at which the particular strength of the first magnetic field and the second magnetic field was determined. What this means is that what is taken as the measured value $W_t(\vec{y}_i)$ for the specimen is the value measured at time t that was measured while the field strengths that are present at point $\vec{y}_i$ during the measurement in step 102 were being generated. The de-convolution of the reference response function from the specimen distribution can then be performed as described in step 104. As was described in step 104, temporally Fourier transformed measured values $W_n(\vec{y}_i)$ for the specimen may also be used. The measured values $W_t(\vec{y}_i)$ for the specimen that are determined in the present case would then simply have to be temporally Fourier transformed.

Determination of the reference response function in this way has the advantage that, particularly when an extensive spherical specimen distribution is being used, the specimen distribution can be looked upon as a mathematical delta function when the reference response function is being de-convoluted. What this means is that in equation (2) the specimen distribution $P(\vec{s})$ can be replaced by a delta function, which means that the measured values $W_t(\vec{y}_i)$ or $W_n(\vec{y}_i)$ for the specimen that are measured in the given case are equal to the values $G_t(\vec{y}_i)$ and $G_n(\vec{y}_i)$ respectively of the reference response function. The reference response function can thus be determined with a particularly small amount of computing work. A further advantage is the fact that the use of a reference response function determined in this way gives reconstructed images of the examination zone in which spatial Fourier transforms of the reconstructed distribution of magnetic particles of different space-frequencies are reconstructed to the same quality, the result of which there is a further improvement in the quality of the image as a whole.

In the last-mentioned embodiment, the sensitivity of the receiving coil 7 has to be allowed for in the measured values for the specimen. If the specimen distribution had really been positioned at a point $\vec{y}_i$, measured values for the specimen that are assigned to the point $\vec{y}_i$, would, due to the sensitivity profile of the receiving coil 7, have been of different values than those that were actually measured, because the specimen distribution was situated at a different point, preferably in the center of the examination zone. Allowance is made for this by for example multiplying the measured values for the specimen by the sensitivity factor that represents the size ratio between measured values for the specimen that, if they had been measured with an ideal receiving coil, would have been the same and that would have been measured if the specimen distribution had been arranged at the point $\vec{y}_i$ and at the point at which the specimen distribution was actually positioned.

The invention claimed is:

1. A method of determining a spatial distribution of magnetic particles in an examination zone, the method comprising:
   a) generating measured values by generating a first magnetic having a pattern of magnetic field strength in space such that a first sub-zone of lower magnetic field strength and a second sub-zone of higher magnetic field strength are produced in the examination zone,
   changing the positions in space of the two sub-zones in the examination zone, thus causing a local change in the magnetization of the particles,
   acquiring measured values that depend on the magnetization in the examination zone, which has been affected by the change in the positions of the two sub-zones,
   b) providing a reference response function by means of which measured values can be determined mathematically from a spatial distribution of magnetic particles, the reference response function being determined by de-convoluting at least one extensive specimen distribution by means of at least one extensive magnetic specimen distribution, and
   c) reconstructing the spatial distribution ($C(\vec{x})$) of magnetic particles in the examination zone from the measured values by means of the reference response function provided.

2. A method as claimed in claim 1, wherein the reference response function is determined in step b) by the following steps:
   positioning the specimen distribution at different points in the examination zone, measured values for the specimen being generated in step a) at each point at which the specimen distribution is positioned,
   determining the reference response function by de-convoluting the specimen distribution by means of the measured values for the specimen.

3. A method as claimed in claim 2, wherein the de-convoluting comprises spatially Fourier transforming the measured values for the specimen and the specimen distribution, complex conjugating the spatially Fourier transformed specimen distribution, forming a quotient function by dividing the spatial Fourier transform of the measured values for the specimen by the complex conjugated spatial Fourier transform of the specimen distribution, and spatially Fourier back-transforming the quotient function, the spatially Fourier back-transformed quotient function being the reference response function.

4. A method as claimed in claim 2, wherein
before the de-convoluting, applying a transformation to the measured values for the specimen that includes a Fourier transformation and that transforms the measured values for the specimen in such a way that the number of transformed measured values for the specimen is smaller than the number of non-transformed measured values for the specimen, and wherein
the de-convoluted reference response function is temporally Fourier back-transformed or, before the reconstructing the spatial distribution, applying the transformation to the measured values for the specimen to the measured values that are generated in step a).

5. A method as claimed in claim 2, wherein, after the generation of the measured values for the specimen, the following steps are performed:
Fourier transforming temporally the measured values for the specimen,
forming datasets, each dataset containing solely temporally Fourier transformed measured values for the specimen of one time-frequency and the data in the dataset depending on the point at which the specimen distribution was positioned in the examination zone during the generation of the given measured value for the specimen,
generating matching values for each dataset by in each case matching a linear combination of trigonometric function to the temporally Fourier transformed measured values for the specimen in the given dataset, the trigonometric functions being dependent on the points at which the specimen distribution was positioned in the examination zone during the generation of the measured values for the specimen, wherein the convoluted reference response function is temporally Fourier back-transformed or the measured values generated in step a) are temporally Fourier transformed before the reconstruction in step c).

6. A method as claimed in claim 5, wherein the reference response function is convoluted from the specimen distribution by means of the matching values and by means of the temporally Fourier transformed measured values for the specimen.

7. A method as claimed in claim 5, wherein trigonometric functions that are used to determine matching values for a dataset that contains temporally Fourier transformed measured values for the specimen of a higher time-frequency, have a higher space-frequency than trigonometric functions that are used to determine matching values for a dataset that contains temporally Fourier transformed measured values for the specimen of a lower time-frequency.

8. A method as claimed in claim 2, wherein, after the generating of the measured values for the specimen, determining intermediate values, the intermediate values corresponding to measured values for the specimen that would have been measured if, when the measured values for the specimen were generated, the specimen distribution had been positioned at a point that was located between those points in the examination zone at which the specimen distribution was actually positioned during the generation of the measured values for the specimen, and accounting for measured values for the specimen that were measured while the specimen distribution was situated at points in the examination zone that were located adjacent to a point for which the intermediate values are to be determined, and de-convoluting reference response function from the specimen distribution by means of the measured values for the specimen and the intermediate values.

9. A method as claimed in claim 2, further comprising: providing a transfer function, so that when applied to measured values for the specimen that were measured while the specimen distribution was positioned at a point in the examination zone, the transfer provides transfer values that correspond to measured values for the specimen that would have been measured if the specimen distribution had been located at some other point in the examination zone; applying the transfer function to the measured values for the specimen to determined the transfer values; and de-convolving the reference response function from the specimen distribution by means of the measured values for the specimen and the transfer values.

10. A method as claimed in claim 1, wherein a plurality of specimen distributions are used for the determination of the reference response function, with different specimen distributions having different space-frequencies, and the following steps being performed for each specimen distribution:
positioning of the specimen distribution at different points in the examination zone, measured values for the specimen being generated in step a) for each point at which the specimen distribution is positioned,
determining a preliminary reference response function by de-convoluting the given specimen distribution by means of the measured values for the specimen, the preliminary reference response functions being combined into one reference response function and the specimen distributions being of a form such that measured values for the specimen that are larger than values for the noise caused by the method claimed in claim 1 are generated for each space-frequency in one or more preset ranges of space-frequencies.

11. A method as claimed in claim 1, wherein, in step a), the change in the positions in space of the two sub-zones in the examination zone is performed by generating a second magnetic field that is variable over time, and wherein the following steps are performed to determine the reference response function in step b):
determining the strength of the first magnetic field at different points in the examination zone,
determining the strength, that is variable with time, of the second magnetic field that is used to change the positions in space of the two sub-zones, at those points at which the strength of the first magnetic field was determined,
positioning of the extensive specimen distribution at any desired point in the examination zone
generating measured values for the specimen for each point at which the strengths of the first magnetic field and the second magnetic field were determined, by the following steps
i) generating a homogeneous magnetic field of the strength that was determined for the first magnetic field at the point,
ii) generating a second magnetic field that is variable over time and is of the strength that was determined for the field that is variable over time at the given point,
iii) acquiring measured values for the specimen that depend on the magnetization that is affected by the change in the positions of the two sub-zones, and
determining the reference response function by de-convoluting the reference response function from the specimen distribution by means of the measured values for the specimen.

12. An apparatus, comprising:
- at least one first magnetic means for generating a first magnetic field that is constant over time and has a pattern of magnetic field strength in space such that a first sub-zone of lower magnetic field strength and a second sub-zone of higher magnetic field strength are produced,
- at least one second magnetic means, for changing the positions in space of the two sub-zones in the examination zone, thus causing a local change in the magnetization of the particles,
- at least one acquisition means for the acquisition of measured values that depend on the magnetization in the examination zone, which is affected by the change in the positions of the two sub-zones,
- at least one extensive specimen distribution,
- at least one reconstruction means for determining a reference response function by deconvoluting the extensive specimen distribution by means of the extensive specimen distribution and for reconstructing the spatial distribution ($C(\vec{x})$) of magnetic particles in the examination zone from the measured values,
- a control unit for controlling the at least one first magnetic means, the at least one means for changing the positions in space of the two sub-zones, the at least one acquisition means and the at least one reconstruction means to perform the steps of claim 1.

13. An apparatus as claimed in claim 12, wherein the apparatus has a positioning means for positioning the specimen distribution at different points in the examination zone, the positioning means being controllable by the control unit to perform the steps of:
- positioning of the specimen distribution at different points in the examination zone, measured values for the specimen being generated in step a) at each point at which the specimen distribution is positioned; and,
- determining the reference response function by de-convoluting the specimen distribution by means of the measured values for the specimen.

14. A computer program stored on anon-transient computer readable medium for a control unit for controlling the at least one first magnetic means, the at least one means for changing the positions in space of the two sub-zones, the at least one acquisition means, the positioning means and the at least one reconstruction means of an apparatus as claimed in claim 13 for performing the method by the steps of:
- positioning of the specimen distribution at different points in the examination zone, measured values for the specimen being generated in step a) at each point at which the specimen distribution is positioned and,
- determining the reference response function by de-convoluting the specimen distribution by means of the measured values for the specimen.

15. A computer program stored on a non-transient computer readable medium for a control unit controlling the at least one first magnetic means, the at least one means for changing the positions in space of the two sub-zones, the at least one acquisition means and the at least one reconstruction means of an apparatus as claimed in claim 12.

16. A method of determining a reference response function for a method as claimed in claim 1, wherein at least one extensive specimen distribution is used for determining the reference response function.

* * * * *